(12) United States Patent
Kwant et al.

(10) Patent No.: US 6,515,115 B1
(45) Date of Patent: Feb. 4, 2003

(54) MEMBRANE FILTRATION

(75) Inventors: Gerard Jan Kwant, Nootdorp (NL); Pieter Johannes Gerrit De Zwarte, Gouda (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 09/647,371

(22) PCT Filed: Apr. 14, 1999

(86) PCT No.: PCT/EP99/02645

§ 371 (c)(1),
(2), (4) Date: Nov. 22, 2000

(87) PCT Pub. No.: WO99/53015

PCT Pub. Date: Oct. 21, 1999

(30) Foreign Application Priority Data

Apr. 14, 1998 (NL) ............................................ 98201209

(51) Int. Cl.[7] .......................... C07H 17/08; C07G 11/00
(52) U.S. Cl. ......................................... 536/6.5; 536/16.8
(58) Field of Search .................................. 536/6.5, 16.8

(56) References Cited

U.S. PATENT DOCUMENTS

| | | | |
|---|---|---|---|
| 5,468,847 A | 11/1995 | Heilmann et al. | 530/413 |
| 5,503,750 A | 4/1996 | Russo et al. | 210/641 |
| 5,616,595 A * | 4/1997 | Chu et al. | 514/344 |
| 5,716,526 A | 2/1998 | Kelemen et al. | 210/650 |

FOREIGN PATENT DOCUMENTS

| | | |
|---|---|---|
| DE | A-277 088 | 7/1914 |
| EP | 0 327 342 A | 8/1989 |
| EP | 0 363 896 A | 4/1990 |
| EP | 0 522 517 A1 | 1/1993 |
| RU | 2 090 598 C | 9/1997 |

* cited by examiner

Primary Examiner—Louise N. Leary
(74) Attorney, Agent, or Firm—Morrison & Foerster LLP

(57) ABSTRACT

The invention relates to a process for isolating a desired water-soluble product from a fermentation broth wherein the broth is circulated along a ceramic membrane, and wherein a trans-membrane pressure of at least 1.5 bar is applied, whereupon an aqueous solution containing the desired product traverses the membrane, and is subsequently collected. Advantageously, during this filtration process the temperature of the broth is maintained at 20 to 50° C., preferably at 30 to 45° C. According to the invention, a decreased process time and a higher capacity and efficiency of the filtration are obtained.

19 Claims, No Drawings

MEMBRANE FILTRATION

RELATED CASES

This application is a national stage filing of International Application No. PCT/EP99/02645 filed Apr. 14, 1998. The contents of this document are expressly incorporated herein by reference.

FIELD OF THE INVENTION

The invention relates to a process for isolating a desired water-soluble product from a fermentation broth.

BACKGROUND OF THE INVENTION

Nowadays fermentation processes for preparing chemical compounds play an increasing role in chemistry. As this kind of process is highly selective, environmentally attractive and leads to high product yields, even industrial preparations are carried out this way.

After a fermentation is completed, the desired product needs to be isolated from the fermentation broth. Conventionally, this is done by first separating the aqueous phase from the cell material in a cake filtration step, followed by an extraction or adsorption of the product from the filtrate. Often, however, such a cake filtration step is accompanied by a significant loss of desired product. This is mainly due to the fact that the filter cake cannot be washed out sufficiently and that a rather large amount of the product remains in the filter cloth. In practice, it is observed that the efficiency and the capacity of the filtration process strongly depend on the quality of the fermentation broth. In addition, "dissolved" proteins and cell debris present in the filtration broth are insufficiently removed from the aqueous phase of the fermentation broth by the cake filtration. This has the effect that subsequent downstream processes suffer from contamination with proteins, and their capacity is diminished.

In order to overcome the above problems in the work up procedure of fermentation broths, it has been proposed to make use of other filtration methods, such as membrane filtration. The membranes used for these purposes are usually polymeric membranes, such as polysulfone membranes.

The advantage of membrane filtration is, that by design less product is lost and a more pure filtrate (permeate) is obtained. The permeate contains significantly less proteins and/or remains of cell material than the filtrate obtained in a conventional cake filtration technique. As a result, the extraction step can be carried out more conveniently, and the overall efficiency of the process is increased.

In the East German patent application DD-A-277 088, a process for isolating benzylpenicillin from a microbiological broth is described. The process involves a conventional cake filtration step to remove the biomass, and a subsequent ultrafiltration step, wherein the proteins present in the filtrate of the first filtration are separated. The product of the ultrafiltration is concentrated to 5% of its volume, and the desired benzylpenicillin is isolated therefrom by extraction.

A membrane filtration process for broth filtration usually comprises three steps. In practice, particularly in a continuous process, the transition from one step to another may not be so clearly discernible. It often happens that two or all of these steps are carried out at the same time. However, for clarity's sake it is useful to draw this distinction. The first step is a concentration of the composition that is to be filtered. Such a concentration step can suitably be carried out, by circulating the broth along the membrane surface while a pressure gradient is maintained over the surface (often referred to as cross-flow filtration). In the second step, the obtained concentrated product is washed during cross-flow filtration in a dialysis step. This means that a flow of solvent is added to the circulating flow of broth. In case the filtered product is a fermentation broth this solvent will generally be water. In the third step, the obtained filtered permeate is concentrated further during cross-flow filtration to a suitable extent.

In a process involving a membrane filtration step, it is necessary to control the flow conditions of the retentate (the residue of the filtration) along the membrane by applying a high cross-flow velocity (i.e. a linear flow velocity parallel to the plane of the membrane), in order to maximise the flux (capacity) of the process. However, in practice a number of problems arises upon trying to maintain a fast flow of the retentate after it has been concentrated. These problems are particularly encountered in case a fermentation broth having high contents (3–10%) of cell debris and proteins is to be filtered.

Due to an increased viscosity, which is observed at high concentration factors, the axial pressure drop, which is a measure for the energy required in the process, increases as well. In large scale applications, centrifugal pumps are applied and the capacity thereof decreases as a result of the increased axial pressure drop. Due to the pseudoplastic nature of the involved materials under these conditions, the viscosity increases even more, which in its turn amplifies the flow decrease further. Furthermore, a lot of heat is generated which is undesired in cases wherein the desired product is unstable at high temperatures. Therefore, in order to keep the temperature low and to avoid product degradation, a large and expensive cooling device is necessary.

Also, it is desired to minimise the time needed to complete the filtration process in order to prevent degradation and contamination of the desired product. The available measures to minimise the filtration time are increasing the filter membrane surface, or demanding an increasing specific capacity. The specific capacity indicates how much of the desired product permeates a certain surface area of the membrane per time unit ($l/m^2 \cdot h$). Said capacity may be increased by applying a high trans-membrane pressure, which is the driving force behind the filtration. A disadvantage of applying a high trans-membrane pressure is that it usually leads to a higher retention of the desired product, i.e. a large amount of product that does not permeate the membrane, which leads to an inefficient process. Furthermore, the application of tubular polymeric membranes in such cases may not be possible, as this type of membrane wears out too much under these conditions.

It has presently been found that the above problems can be overcome by using a ceramic membrane and by controlling the process conditions in a surprising manner.

The use of ceramic membranes has been reported in the prior art for diverse separations of desired products from a fermentation broth.

In EP 0 522 517 A1 an α-alumina microporous membrane is used for the separation of methyl glucoside from a fermentation broth. In a first step the broth is concentrated, whereafter the water-insoluble methyl glucoside is dissolved by the addition of methanol, whereafter the methyl glucoside containing solution passes the membrane and the antibiotic is recovered.

A similar technique is described in U.S. Pat. No. 5,616,595 for the separation of cyclosporin A from a fermentation broth.

According to the Russian patent publication No. 2090598 ceramic filter elements can be applied for the filtration of must in the production of wine.

DESCRIPTION OF THE INVENTION

The present invention relates to a process for isolating a desired water-soluble product from a fermentation broth wherein the broth is circulated along a ceramic membrane, and wherein a trans-membrane pressure of at least 1.5 bar is applied, whereupon an aqueous solution containing the desired product traverses the membrane, and is subsequently collected.

The process according to the invention has the advantage that a very short filtration time can be realised without the known problem of a high retention of the desired product. Thus, the present filtration process is highly efficient. Surprisingly, a high trans-membrane pressure can be applied in a process according to the invention without encountering a high retention of the desired product. Also, the temperature can very suitably be controlled at a desired value without leading to viscosity problems and without leading to breakdown of the, often thermally unstable, desired product. Moreover, in a process according to the invention it is not necessary to carry out a conventional filtration of the fermentation broth, prior to subjecting it to the membrane filtration, as has been described in DD-A-277 088.

The fermentation broth can be obtained from any fermentation process. In such a process, a suitable micro-organism strain is fermented by adding a carbon source, a nitrogen source, other nutrients and air to the broth. Typical operation procedures and recipes may be found in the literature. After the fermentation process has been completed to a desired extent, the broth will comprise cell material as well as proteins and the desired product. Also, different contaminants may be present. It is preferred that the broth is obtained from a fermentation process wherein an anti-infective compound is prepared. Examples of such compounds are various β-lactams and compounds such as erythromycin and nystatin.

Examples of β-lactams in this regard are β-lactams wherein the β-lactam nucleus is attached to a suitable side chain, such as penicillin G, penicillin V, adipyl-7-aminocephalosporanic acid, adipyl-7-aminodesacetoxycephalo-sporanic acid, clavulanic acid, cephalosporin C, Ampicillin, Amoxycillin, Cephalexin, Cephaclor and Cephadroxyl. Possibly also suitable are β-lactam nuclei, such as 6-aminopenicillanic acid (6-APA), 7-aminocephalosporanic acid (7-ACA), 3-chloro-7-aminodesacetoxydesmethylcephalosporanic acid (3-CI,7-ACCA), 7-aminodesacetylcephalosporanic acid (7-ADAC), and 7-aminodesacetoxycephalosporanic acid (7-ADCA). Most preferred are fermentation broths obtained from processes for preparing penicillin G, penicillin V, cephalosporin C, acyl-7-ADCA or acyl-7-ACA. It has been found that a filtering process of one of these fermentation broths benefits significantly of the advantages of the invention. Even though many of these fermentation broths comprise thermally unstable products, it has been found that in a process according to the invention these thermally unstable products can be isolated from the broth without a significant loss of product.

The membrane that is used in accordance with the invention is a ceramic membrane. This means that it comprises an inorganic material. Preferred materials are metallic oxides, such as α-alumina, γ-alumina and zirconia. The use of membranes of these materials leads to highly efficient filtration processes, wherein only very small amounts of the desired product are lost, if at all, and wherein the desired product is obtained in a very high purity.

Preferably, a ceramic membrane is used, which has an average pore size of 4 to 100 nm, more preferably of 20 to 50 nm. The use of a membrane having a pore size within these ranges has been found to lead to a highly selective and efficient membrane filtration process.

During the circulating of the broth along the membrane (cross-flow filtration), it will become concentrated, as increasing amounts of the fluids present in the broth permeate through the membrane. A suitable extent of the concentration is 1.5, preferably 2 times. Said concentration can most advantageously be performed at increased temperatures, preferably at a temperature higher than 20° C., more preferably higher than 30° C. The upper limit of the temperature during concentration will for practical reasons generally be 50° C., preferably 45° C.

In accordance with the invention, it has been found that the viscosity of the broth does not reach unacceptable high values. When the concentration factor is two, typical maximum values are, 337 mpa·s at a shear of 100 s$^{-1}$, 197 mPa·s at a shear of 500 s$^{-1}$, and 156 mPa·s at a shear of 1000 s$^{-1}$. Thus, no additional, expensive equipment is required to carry out the circulation at a sufficient cross-flow velocity.

It is possible that the cross-flow velocity shows a slight fluctuation during a process according to the invention and reaches values of 2–4 m/s. However, said velocity is preferably maintained at a value of at least 5, more preferably 6 m/s. It is preferred that the upper limit of said velocity is 10, more preferably 8 m/s. When said velocity is chosen within the specified ranges, the filtration process has a very high capacity. It has presently proven to be possible to keep the velocity high even when the concentration is carried out to a large extent.

After the retentate has been concentrated to the desired extent, it is preferred that water is added to the circulating broth (dialysis). Preferably, such an amount of water is added, that the broth is diluted 1.5–4 times, more preferably 2–3 times. By this addition of water to the retentate, the yield, and consequently the efficiency, of the filtration process is increased. Amounts of the desired product in the retentate can yet be recovered by this dilution step, which comprises the addition of water to the retentate.

A great advantage of the process of the invention is that a very short process time can be achieved, without the occurrence of the known problem of a high retention of the desired product. Thus, in accordance with the invention the trans-membrane pressure is higher than 1.5 bar. In the context of the invention, the trans-membrane pressure is defined as the difference in the average on the retentate side and the average pressure of the permeate side of the membrane. In a preferred embodiment the trans-membrane pressure is from 2.5 to 7.5, preferably from 4 to 6 bar.

In accordance with a highly preferred embodiment of the invention, the trans-membrane pressure is initially lower than the above specified pressure. Suitable initial trans-membrane pressures are chosen between 1 and 2.5 bar. The period of time during which this initial trans-membrane pressure is applied is relatively short. In general, said period will not be longer than 10%, preferably not longer than 8% of the total filtration time. In most practical cases, dependent on the amount of fermentation broth to be filtered, said period will be approximately 10 minutes.

This embodiment is advantageous in that fouling of the membrane occurs significantly less than when the eventually desired, high trans-membrane pressure is applied from the start of the process. Because of this, the lifetime of the membrane is increased, i.e. the period of time, wherein the same membrane can be used without it having to be cleaned, is increased. Also, the capacity of the filtration process is higher, and the selectivity greater. Without wishing to be bound by theory, it is believed that these advantages are achieved because of a protein gel layer on the retentate side of the membrane, which is deposited during the initial period wherein a lower trans-membrane pressure is applied.

The inlet pressure of the retentate in a process according to the invention will, depending on the stage during the process, vary between 1 and 8 bar. The axial pressure drop of the retentate will, also depending on the stage during the process, vary between 0 and 3.5 bar. The specific flux may vary from 200 $l/m^2 \cdot h \cdot bar$ to 50 $l/m^2 \cdot h \cdot bar$ and back to 200 $l/m^2 \cdot h \cdot bar$ during the course of the process.

On the permeate side of the membrane, a continuous flow will usually be maintained in order to collect the permeate, and in particular the desired product present therein. After the permeate has been collected, it can advantageously be concentrated. Preferred extents of concentration of the permeate are from 1.5 to 7, more preferably from 2 to 5 times. In order to recover the desired product present in the concentrated permeate, conventional work up procedures will generally be carried out. A suitable example of such a work up procedure is an extraction.

A process in accordance with the invention can be carried out either batch-wise or continuously. It is preferably carried out as a continuous process.

The invention will be further elucidated by the following, non-restrictive examples.

EXAMPLE 1

156 kg of a penicillin fermentation broth was fed from a stirred feed tank to an membrane filtration (MF) system. Said system comprised a Membranlox SCT 3P19 membrane having a surface of approximately 0.9 $m^2$ and an average pore size of 50 nm.

The system was de-aerated and the filtration process was started at the following conditions:

| | |
|---|---|
| temperature | 21° C. |
| circulation flow feed tank | 2.5 $m^3/h$ |
| circulation flow filtration loop | 35 $m^3/h$ |

(cross-flow velocity was 6 m/s).

After 65 l of permeate was removed ($\alpha$=1.67 (concentration factor), $\beta$=0.4 (dilution factor)), the circulation flow of the filtration loop had decreased to 17 $m^3/h$, which corresponds to 2.9 m/s cross-flow velocity. The permeate flow decreased to 70 $l/m^2h$ at a trans-membrane pressure of 4 bar. The concentration factor was 1.67. Further concentration was not possible. Diafiltration was started keeping $\alpha$ constant, the cross-flow velocity increased again up to 5.5 m/s, the permeate flow remained constant at 72 $l/m^2 \cdot h$. The dilution factor was 1.72.

The total process time was 250 minutes.

EXAMPLE 2

154 kg of a penicillin fermentation broth was fed from a stirred feed tank to the same MF system as was used in Example 1.

The system was de-aerated and the filtration process was started at the following conditions:

| | |
|---|---|
| temperature | 40° C. |
| circulation flow feed tank | 2.5 $m^3/h$ |
| circulation flow filtration loop | 35 $m^3/h$ |

(cross-flow velocity was 6 m/s)

After 74 l of permeate was removed ($\alpha$=1.92, $\beta$=0.48), the circulation flow of the filtration loop had only slightly decreased to 26 $m^3/h$. The permeate flow decreased to 94 $l/m^2h$ at a concentration factor of 2.0, and a trans-membrane pressure of 4 bar.

Directly after starting the diafiltration in which $\alpha$ was kept constant, the cross-flow velocity increased again up to 5.9 m/s, and the permeate flow was controlled to be 110 $lm^2h$. The dilution factor was 1.85.

The total process time was 180 minutes.

EXAMPLE 3

177 kg of a penicillin fermentation broth was fed from a stirred feed tank to the same MF system as was used in Example 1.

The system was de-aerated and the filtration process was started at the following conditions:

| | |
|---|---|
| temperature | 36° C. |
| circulation flow feed tank | 2.5 $m^3/h$ |
| circulation flow filtration loop | 35 $m^3/h$ |

(cross-flow velocity was 6 m/s)

After 90 l of permeate was removed ($\alpha$=2.04, $\beta$=0.51), the circulation flow was 6 m/s. The permeate flow of 511 $l/m^2h$ at the start of the concentration, decreased to 124 $l/m^2h$ at the end of the concentration. The concentration factor was 2.04, and the trans-membrane pressure was 5 bar.

After starting the diafiltration in which (x was kept constant, the permeate flow very slowly increased and was controlled to be 255 $l/m^2h$. The trans-membrane pressure slowly went down to 3.8 bar at the end of the process. The dilution factor was 2.02.

The total process time was 134 minutes.

What is claimed is:

1. A process for isolating a desired water-soluble product from a fermentation broth comprising circulating the broth along a ceramic membrane while applying during at least a substantial time of the process a trans-membrane pressure of at least 1.5 bar, wherein a permeate containing the desired water soluble product traverses the membrane, and the permeate is collected, subsequently adding water to the remaining broth, and collecting any further permeate containing the water soluble product.

2. A process according to claim 1, wherein the broth is concentrated during the circulating step at a temperature between 20 and 50° C.

3. A process according to claim 2, wherein the temperature is from 30 to 45° C.

4. A process according to claim 1, wherein the cross-flow velocity is from 5 to 10 m/s.

5. A process according to claim 1, wherein the ceramic membrane comprises a metallic oxide material.

6. A process according to claim 5, wherein the ceramic membrane has an average pore size of 4–100 nm.

7. A process according to claim 1, wherein the transmembrane pressure is 2.5–7.5 bar.

8. A process according to claim 7, wherein the transmembrane pressure is initially 1–2.5 bar.

9. A process according to claim 2, wherein water is added to the remaining broth, once said broth has been concentrated about 1.5 times.

10. A process according to claim 9, wherein an amount of water is added in the adding step, such that the broth is diluted 1–4 times.

11. A process according to claim 10, wherein the permeate is concentrated 1.5–7 times.

12. A process according to claim 1, wherein the fermentation broth is obtained from a fermentation process wherein an anti-infective compound is prepared.

13. A process according to claim 12, wherein the anti-infective compound is chosen from the group consisting of erythromycin, nystatin, adipyl-7-aminocephalosporanic acid, adipyl-7-aminodesacetoxycephalosporanic acid, penicillin G, penicillin V, cephalosporin C, and isopenicillin N.

14. A process according to claim 6, wherein the ceramic membrane has an average pore size of 20–50 nm.

15. A process according to claim 7, wherein the transmembrane pressure is 3–6 bar.

16. A process according to claim 2, wherein water is added to the remaining circulating broth, once said broth has been concentrated about 2 times.

17. A process according to claim 10, wherein the broth is diluted 1.5–3 times.

18. A process according to claim 11, wherein the permeate is concentrated 2–5 times.

19. A process according to claim 4, wherein the cross-flow velocity is from 6 to 8 m/s.

* * * * *